United States Patent [19]

Gabrielsen

[11] Patent Number: 4,552,980

[45] Date of Patent: Nov. 12, 1985

[54] DYE PRECURSORS AND THEIR USE IN PHOTOGRAPHIC MATERIALS AND PROCESSES

[75] Inventor: Rolf S. Gabrielsen, Rochester, N.Y.

[73] Assignee: Eastman Kodak Company, Rochester, N.Y.

[21] Appl. No.: 488,222

[22] Filed: Apr. 25, 1983

Related U.S. Application Data

[62] Division of Ser. No. 373,915, May 3, 1982, Pat. No. 4,411,984.

[51] Int. Cl.[4] .......... C07C 161/00

[52] U.S. Cl. .......... 564/79

[58] Field of Search .......... 564/79

[56] References Cited

U.S. PATENT DOCUMENTS

| | | | |
|---|---|---|---|
| 3,443,943 | 5/1969 | Rogers et al. | 96/29 |
| 3,482,971 | 12/1969 | Bloom et al. | 96/3 |
| 3,622,603 | 11/1971 | Bloom et al. | 260/397.7 |
| 3,938,995 | 2/1976 | Gompf et al. | 96/55 |
| 4,008,043 | 2/1977 | Kalopissis et al. | 564/99 |
| 4,035,184 | 7/1977 | Faul et al. | 96/22 |
| 4,273,860 | 6/1981 | Adin | 430/338 |
| 4,373,017 | 2/1983 | Masukawa et al. | 564/79 |

FOREIGN PATENT DOCUMENTS

| | | |
|---|---|---|
| WO80/01322 | 6/1980 | PCT Int'l Appl. . |
| 1236087 | 6/1971 | United Kingdom . |
| 2012445A | 7/1979 | United Kingdom . |

OTHER PUBLICATIONS

*Research Disclosure,* Item No. 18436.
*Research Disclosure,* Item No. 12617.
*Research Disclosure,* Item No. 17029.
Journal of the American Chemical Society, 92:13, Jul. 1, 1970, pp. 3943-3946.
*Research Disclosure,* Item No. 12543.
*Research Disclosure,* Item No. 16845.
Hackh's Chemical Dictionary, 4th Edition, Julius Grant, editor, McGraw-Hill Book Co. 1969, pp. 27 and 62.

*Primary Examiner*—Charles F. Warren
*Assistant Examiner*—R. A. Picard
*Attorney, Agent, or Firm*—Richard E. Knapp

[57] ABSTRACT

A diphenylamine compound that is a precursor for a phenazine dye comprises, in an ortho position to the amine of the diphenylamine, a sulfonyldiamido group (—$NHSO_2NHR$) that is capable of releasing a sulfonylamine fragment upon oxidation. The diphenylamine compound upon oxidation intramolecularly cyclizes to a phenazine dye. The sulfonylamine fragment is capable of thermally releasing ammonia or an amine. The diphenylamine compound and sulfonylamine fragment are useful in imaging such as in photothermography. Ammonia or an amine thermally released from the sulfonylamine fragment enables imaging in imaging materials that are responsive to ammonia or an amine. The diphenylamine compound also generally is a silver halide developing agent.

1 Claim, No Drawings sponse to the presence of ammonia or an amine is that the photographic silver halide is useful for its high degree of photosensitivity and the image forming material that generates an image in response to the presence of ammonia or an amine, such as a reducible cobalt(III) complex, provides desired image discrimination and image density enhancement.

The new diphenylamine compounds according to the invention in many cases are also silver halide developing agents in photographic materials and processes. If the diphenylamine compound does not produce sufficient development activity, then optional addition of a crossoxidizing developing agent allows adequate development to occur. In many cases, addition of a separate silver halide developing agent is not necessary.

An image in a photographic material according to the invention is developed by heating the exposed photographic material to processing temperature, such as a temperature within the range of about 100° C. to about 200° C., until an image is developed.

DETAILED DESCRIPTION OF THE INVENTION

The new diphenylamine compounds that are precursors for phenazine dyes are useful in a photographic material and process according to the invention. Combinations of such diphenylamine compounds are also useful. Illustrative new diphenylamine compounds according to the invention are represented by the formula:

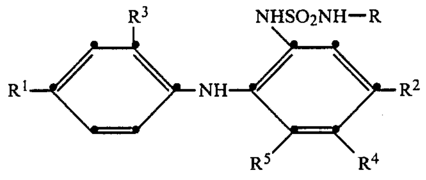

wherein

- $R^1$ is hydrogen, substituted amino, such as alkylamino and dialkylamino containing 1 to 10 carbon atoms, such as methylamino, ethylamino, propylamino and diethylamino, alkyl containing 1 to 20 carbon atoms, such as methyl, ethyl, propyl, decyl and eicosyl, alkoxy containing 1 to 20 carbon atoms, such as methoxy, ethoxy, propoxy, decyloxy and eicosyloxy, aryloxy containing 6 to 20 carbon atoms, such as phenoxy and ethylphenoxy, sulfonamido or carboxamido;
- $R^2$ is hydrogen, alkyl containing 1 to 20 carbon atoms, such as methyl, ethyl, propyl, butyl, decyl and eicosyl, alkoxy containing 1 to 20 carbon atoms, such as methoxy, ethoxy, propoxy, decyloxy and eicosyloxy, sulfonamido, carboxamido, ureido, or halo, such as chloro, bromo and iodo;
- R and $R^3$ are individually hydrogen or alkyl containing 1 to 20 carbon atoms, such as methyl, ethyl, propyl, butyl, pentyl, decyl and eicosyl.
- $R^4$ is hydrogen or a substituent, for example, substituted amino, such as alkylamino and dialkylamino containing 1 to 10 carbon atoms, such as methylamino, ethylamino, propylamino and diethylamino, sulfonyldiamido ($-NHSO_2NHR$), such as $-NHSO_2NH_2$ and $-NHSO_2NH$—t— butyl, aryl containing 6 to 20 carbon atoms, such as phenyl, tolyl and naphthyl, alkyl containing 1 to 20 carbon atoms, such as methyl, ethyl, propyl, butyl, decyl and eicosyl, alkoxy containing 1 to 20 carbon atoms, such as methoxy, ethoxy, propoxy and decyloxy, sulfonamido, carboxamido or halo, such as chloro, bromo or iodo or taken together with $R^5$ represents the carbon and hydrogen atoms necessary to complete an aromatic ring, for example, a 5 to 12 member aromatic ring, such as a phenyl or naphthyl ring.
- $R^5$ is hydrogen or a substituent, for example, alkyl containing 1 to 20 carbon atoms, such as methyl, ethyl, propyl, decyl and eicosyl, aryl containing 6 to 20 carbon atoms, such as phenyl, tolyl and naphthyl, sulfonyldiamido ($-NHSO_2NHR$), such as $-NHSO_2NH_2$ and $-NHSO_2NH$—t—butyl, sulfonamido, carboxamido, halo, such as chloro, bromo and iodo, alkoxy containing 1 to 20 carbon atoms, such as methoxy, propoxy, butoxy and decyloxy, or together with $R^4$ represents the carbon and hydrogen atoms necessary to complete an aromatic ring, such as a phenyl or naphthyl ring.
- $R^4$ and $R^5$ are preferably individually hydrogen or alkyl containing 1 to 20 carbon atoms or together represent the carbon and hydrogen atoms necessary to complete an aromatic ring, such as a phenyl or naphthyl ring.

The diphenylamine compound according to the invention is capable, in oxidized form, of intramolecular reaction to produce a phenazine dye. The substituent groups on the diphenylamine nucleus should not interfere with the desired intramolecular reaction or the release of the desired sulfonylamine fragment. The diphenylamine nucleus should be free of substitution in a position ortho to the amine of the diphenylamine to permit the desired intramolecular reaction.

The terminology "in a position ortho to the amine of the diphenylamine" herein means in a position ortho to the —NH— bridge linking the two aryl groups of the diphenylamine.

The sulfonyldiamido group must be capable of being released upon oxidative ring closure of the diphenylamine to provide a sulfonylamine fragment which, in turn, is capable of thermally releasing ammonia or an amine. The groups on the diphenylamine nucleus should not adversely affect the capability of the sulfonyldiamido group from being released upon oxidative ring closure of the diphenylamine.

The term "thermally releasing", such as in thermally releasing ammonia or an amine, herein means that the sulfonylamine fragment separates into ammonia or an amine and other moieties by means of heat applied to the sulfonylamine fragment.

The terms "alkyl" and "aryl" herein include unsubstituted alkyl, such as unsubstituted methyl, ethyl, propyl or butyl, and unsubstituted aryl, such as unsubstituted phenyl. The terms also include alkyl and aryl that are substituted by groups which do not adversely affect the desired properties of the photographic material, the diphenylamine compound, or the sulfonylamine fragment released upon oxidation. Examples of useful substituted alkyl groups include alkyl substituted by alkoxy, carboxamido, methoxy or methylsulfonamido. Examples of useful substituted aryl include methoxyphenyl, 2,4,6-triisopropylphenyl and tolyl. Aryl herein includes alkaryl such as benzyl, 2,4,6-triisopropylphenyl, 2,4,6-triethylphenyl, and xylyl.

The term diphenylamine herein includes a diphenylamine and a phenylnaphthylamine counterpart to the diphenylamine.

DYE PRECURSORS AND THEIR USE IN PHOTOGRAPHIC MATERIALS AND PROCESSES

This is a divisional application of Ser. No. 373,915, filed May 3, 1982, now U.S. Pat. No. 4,411,984.

BACKGROUND OF THE INVENTION

1. Field of the Invention

This invention relates to a new diphenylamine compound that is a precursor for a phenazine dye. The diphenylamine compound comprises, in an ortho position to the amine of the diphenylamine, a sulfonyldiamido group that is capable of releasing a sulfonylamine fragment upon oxidation. It also relates to preparation of a phenazine dye and a sulfonylamine fragment from such a diphenylamine compound. It further relates to the use of such a new diphenylamine compound in photographic materials for producing silver images and dye images. It also relates to use of such new diphenylamine compounds with imaging materials that are responsive to ammonia or an amine released upon heating.

2. Description of the State of the Art

Photographic materials for producing silver images and dye images are known. The dye image in such materials is generally produced by a coupling reaction in which a developing agent is oxidized upon development of photographic silver halide in the material, followed by reaction of the resulting oxidized form of the developing agent with a coupling agent to produce a dye image. It has been desirable to provide alternative means for producing a dye image, especially a dye image that enhances a silver image, other than by a coupling reaction. The formation of dyes by means of new diphenylamine compounds according to the invention does not require a coupling reaction.

Production of reversal color images, also known as positive dye images, comprising developing a silver image in an imagewise exposed photographic material is also known. Such reversal color images and processes for producing such images are described in, for example, U.S. Pat. No. 4,035,184 and U.S. Pat. No. 3,938,995. These patents describe production of a dye image which includes reaction of a color-forming coupler with the oxidized form of an N,N-dialkyl-p-phenylenediamine. Neither of these patents relate to formation of a dye image by means of oxidation of a dye precursor and releasing of a group that is capable of thermally releasing ammonia or an amine. The present invention also avoids the need for a coupling reaction to produce a dye.

Reducing agents are known which upon oxidation intramolecularly react to form a heterocyclic ring, such as a phenazine ring. The reducing agents are described in, for example, U.S. Pat. Nos. 2,622,603 and 3,482,971. The compounds in these patents (a) lack a sulfonyldiamido group that is capable of releasing a sulfonylamine fragment and (b) lack capability of thermally releasing ammonia or an amine.

Imaging compounds that are responsive to or activated by ammonia or an amine are also known. Examples of such imaging compounds are described in, for example, published patent application WO 80/01322 published June 26, 1980. In such an imaging material phthalaldehyde is an imaging component that forms a dye in response to action by ammonia or an amine released from a cobalt(III) complex. None of these ammonia or amine responsive imaging materials contain a diphenylamine compound comprising a sulfonyldiamido group that is capable of aiding and augmenting imaging upon thermal processing.

The term "photographic material" herein means photographic elements and photographic compositions. For instance, photographic material herein includes photographic elements and photographic compositions comprising photographic silver halide and a dye precursor according to the invention.

SUMMARY OF THE INVENTION

It has been found that in a diphenylamine compound a sulfonyldiamido group, in a position ortho to the amine of the diphenylamine, has the capability of being released upon oxidative ring closure of the diphenylamine to form a phenazine dye and to form a sulfonylamine fragment. The sulfonylamine fragment is capable of thermally releasing ammonia or an amine. Preferably, the sulfonyldiamido group is represented by the formula:

$$-NHSO_2NH-R$$

wherein R is hydrogen or alkyl, such as alkyl containing 1 to 20 carbon atoms.

It has also been found that a phenazine dye and a sulfonylamine fragment, as described above, are prepared by oxidizing the diphenylamine to release the sulfonylamine fragment and intramolecularly cyclize the diphenylamine. Oxidizing the diphenylamine is preferably carried out by means of an oxidizing agent, or a combination of oxidizing agents, selected from the group consisting of ferricyanide, triarylimidazole radicals especially from heat sensitive oxidant types and photooxidant types of triarylimidazoles, fatty acid silver salts, oxidized electron transfer agents, dichromates, oxygen and permanganate oxidizing agents. Following oxidation of the diphenylamine, ammonia or an amine is released from the resulting sulfonylamine fragment by heating the sulfonylamine fragment to a temperature within the range of about 80° C. to about 200° C.

A dye image, preferably a dye image that enhances a silver or dry image, is produced according to the invention by means of a photographic material comprising, in reactive association, preferably in a binder, photographic silver halide and a diphenylamine having, in an ortho position to the amine of the diphenylamine, a sulfonyldiamido group that is capable upon oxidation of the diphenylamine of releasing a sulfonylamine fragment, which, in turn, is capable of thermally releasing ammonia or an amine. The diphenylamine, also upon oxidation, intramolecularly cyclizes to form a phenazine dye. The dye image absorbs radiation in the ultraviolet or visible regions of the electromagnetic spectrum.

A preferred photographic material according to the invention comprises at least one image forming material which generates an image at processing temperature in response to the presence of ammonia or an amine from the sulfonylamine fragment. For example, the photographic material optionally comprises an aromatic dialdehyde, such as o-phthalaldehyde, capable of reacting with ammonia or an amine generated from the sulfonylamine fragment to form a dye. The photographic material also optionally comprises a reducible cobalt(III) complex. An advantage of such photographic materials comprising photographic silver halide and an image forming material that generates an image in re- A carboxamido group herein means an unsubstituted carboxamido group or a carboxamido group that is substituted by a group that does not adversely affect the desired properties of the diphenylamine according to the invention. A carboxamido group herein means, for example, a group represented by the structure:

—NHCO—Z′ wherein

Z′ is a substituent, such as alkyl containing 1 to 25 carbon atoms, for example, methyl, ethyl, propyl, butyl, decyl and eicosyl, and aryl containing 6 to 25 carbon atoms, such as phenyl, tolyl, 2,4,6-triisopropylphenyl, 2,4,6-triethylphenyl, and naphthyl.

A sulfonamido group herein means an unsubstituted sulfonamido group or a sulfonamido group that is substituted by a group that does not adversely affect the desired properties of the diphenylamine according to the invention. A sulfonamido group herein means, for example, a group represented by the structure:

—$NHSO_2Z$ wherein

Z is a substituent, such as alkyl containing 1 to 25 carbon atoms, for example, methyl, ethyl, propyl, decyl and eicosyl, and aryl containing 6 to 25 carbon atoms, such as phenyl, tolyl, 2,4,6-triisopropylphenyl, 2,4,6-triethylphenyl, and naphthyl.

An optimum diphenylamine compound according to the invention will depend upon such factors as the desired image, particular photographic material, processing steps and conditions, particular photographic silver halide in the photographic material, other components in the photographic material and the particular crossoxidizing developing agent. Examples of useful diphenylamine compounds according to the invention include the following:

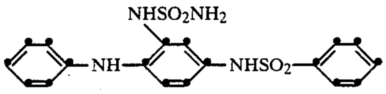

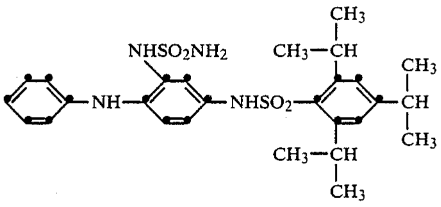

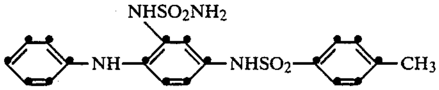

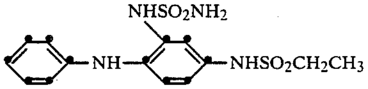

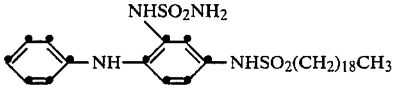

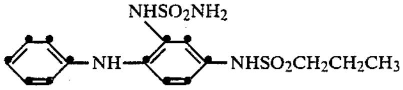

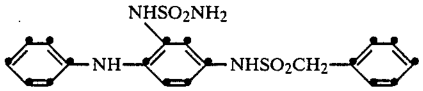

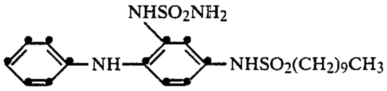

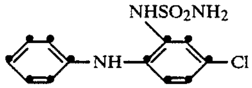

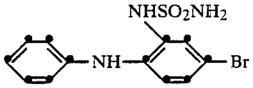

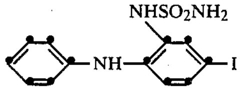

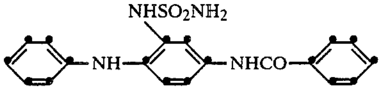

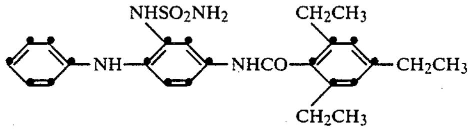

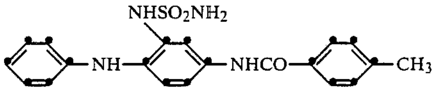

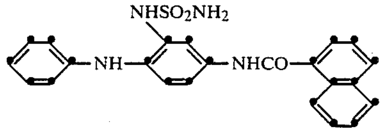

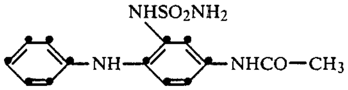

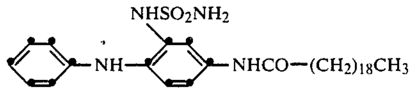

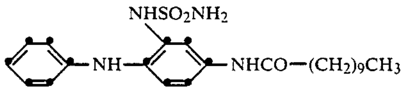

-continued
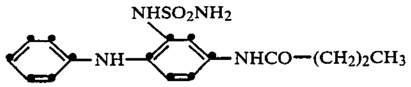
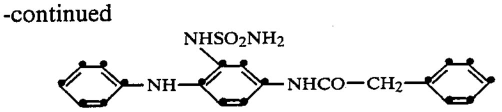
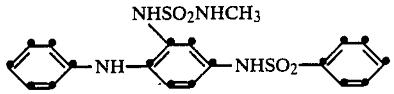
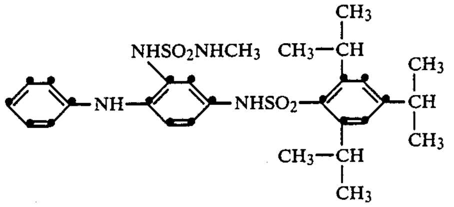
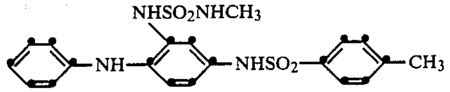
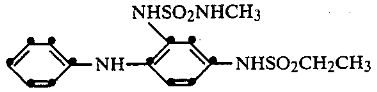
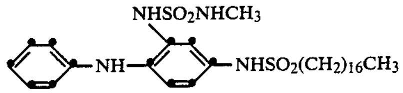
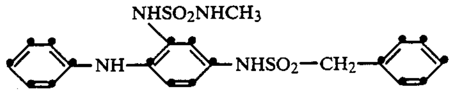
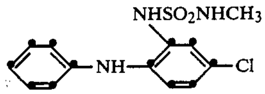
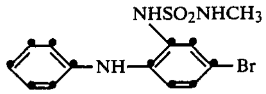
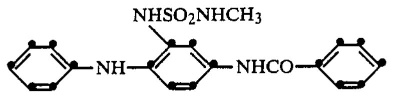
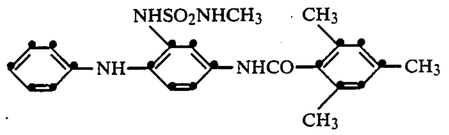
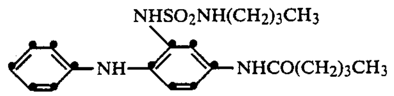
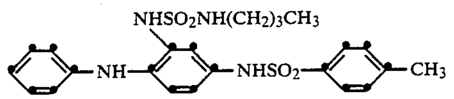
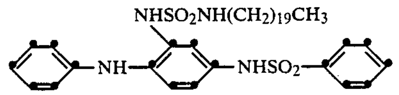
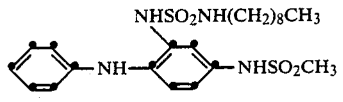
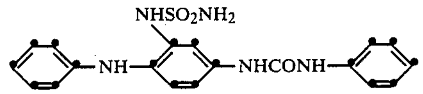
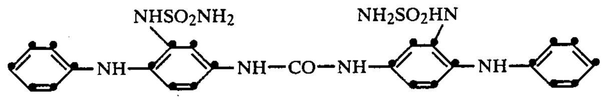
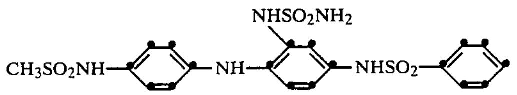
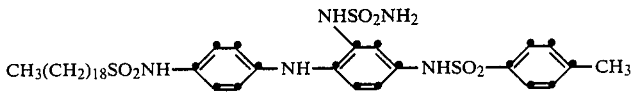
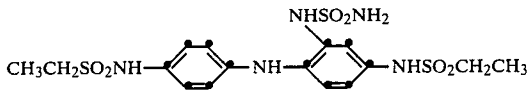
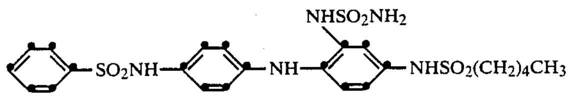
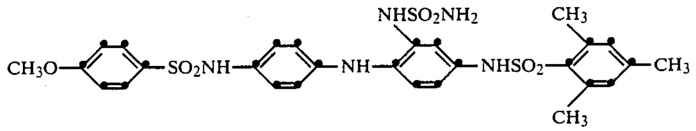

-continued
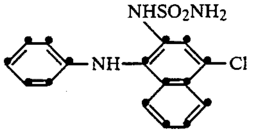
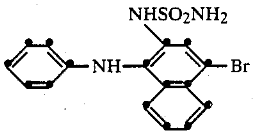
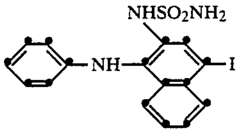
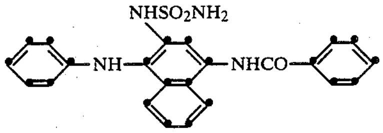
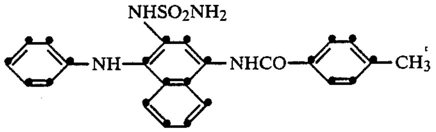
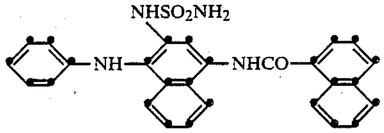
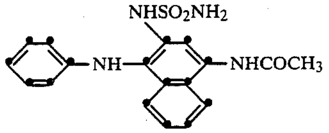
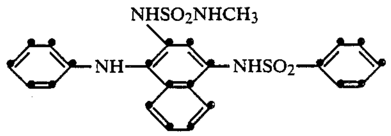
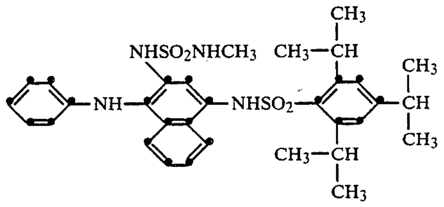
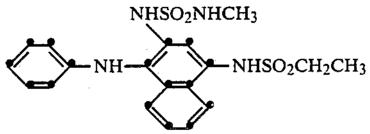
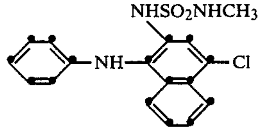
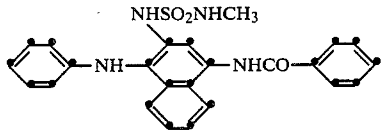
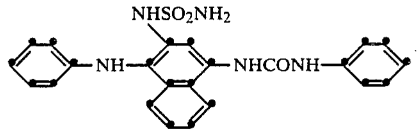
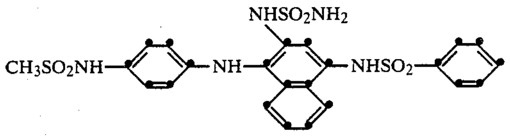
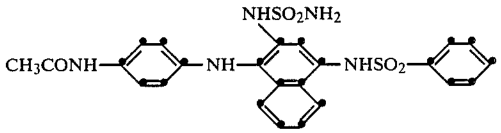
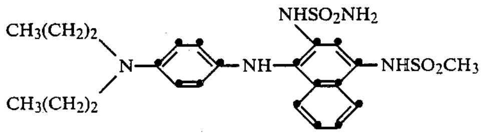
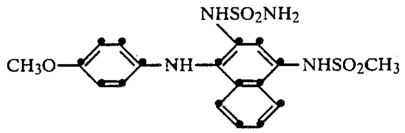
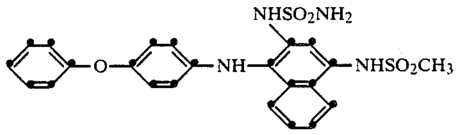
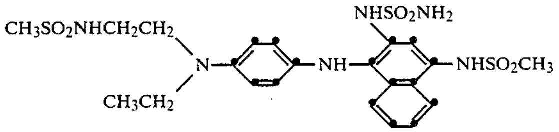
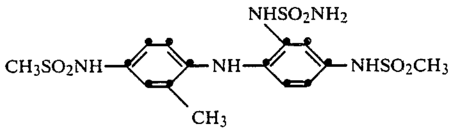

-continued
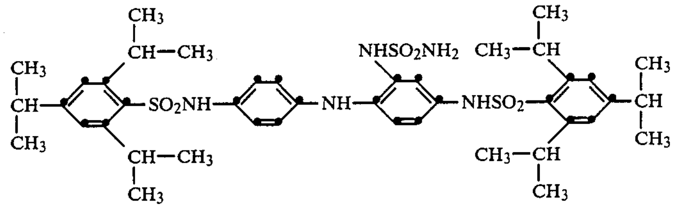
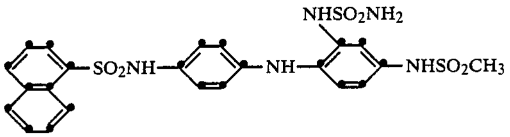
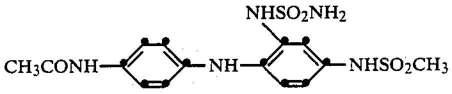
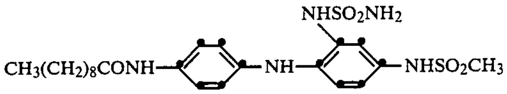
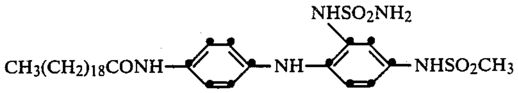
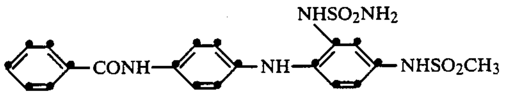
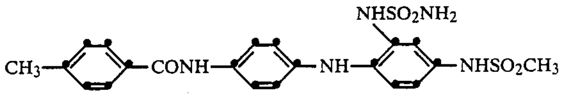
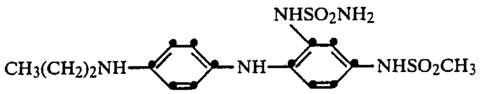
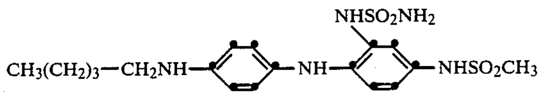
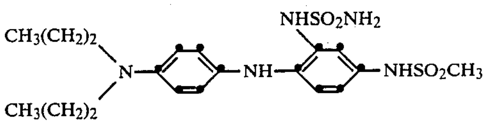
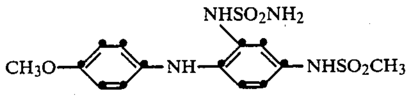
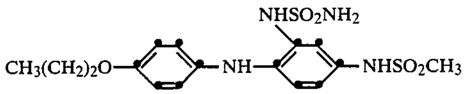
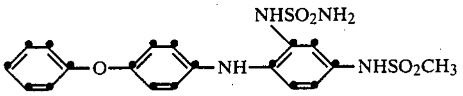
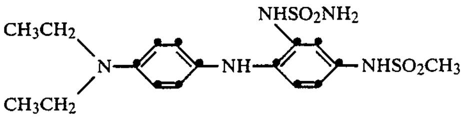
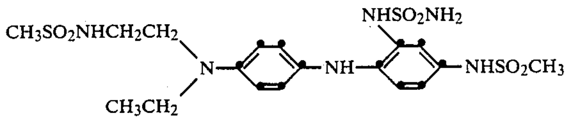
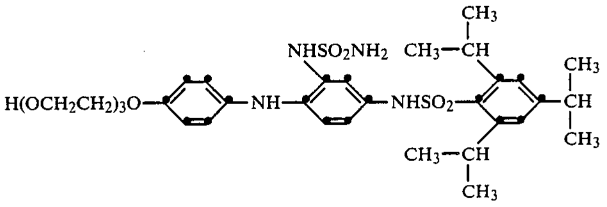
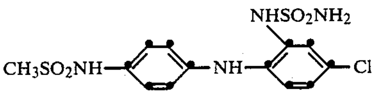
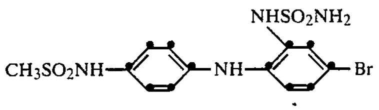
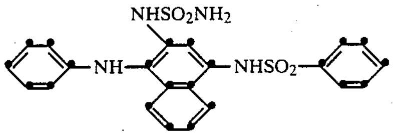
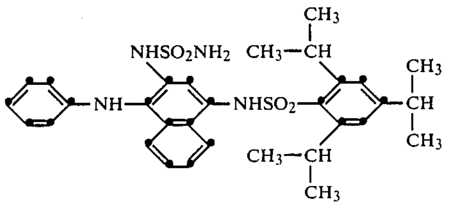
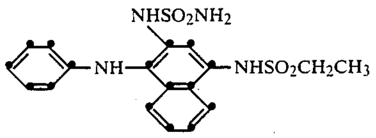

-continued

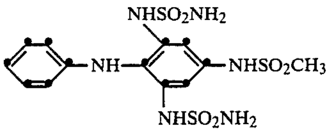

Particularly useful diphenylamines according to the invention include the following:

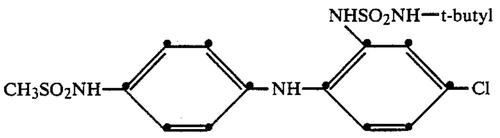

(A)

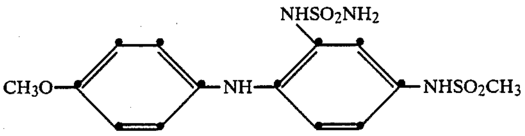

(B)

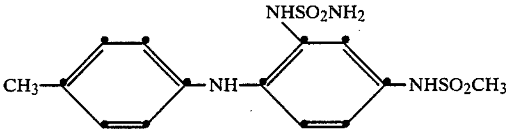

(C)

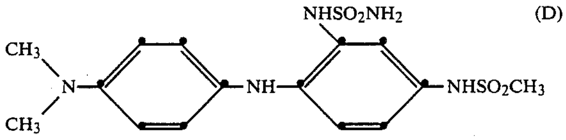

(D)

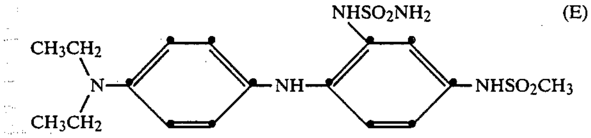

(E)

Combinations of these compounds are also particularly useful.

The diphenylamine compounds according to the invention are prepared by a series of steps. An illustrative process of preparing such diphenylamine compounds is the preparation of sulfonamidodiphenylamine compounds. In such a process the first step involves reaction of an appropriate nitrofluorosulfonamido compound with an appropriate phenylenediamine in the presence of a suitable solvent, such as α-picoline to produce an appropriate nitro-substituted sulfonamidodiphenylamine with the release of hydrogen fluoride. The second step involves hydrogenation in the presence of a suitable catalyst, such as Raney nickel, of the nitro-substituted sulfonamidodiphenylamine to produce an amino compound. The amino compound is reacted with an appropriate sulfonylchloride in the presence of a suitable solvent, such as pyridine to produce the desired diphenylamine dye precursor according to the invention.

The preparation of N-[2-(4-N,N-diethylaminoanilino)-5-methanesulfonamidophenyl]sulfamide:

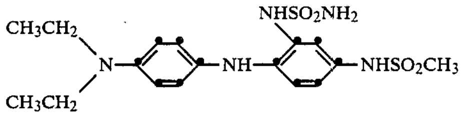

is representative of preparations according to the invention. This preparation is carried out by a series of steps as follows:

The following reaction is carried out:

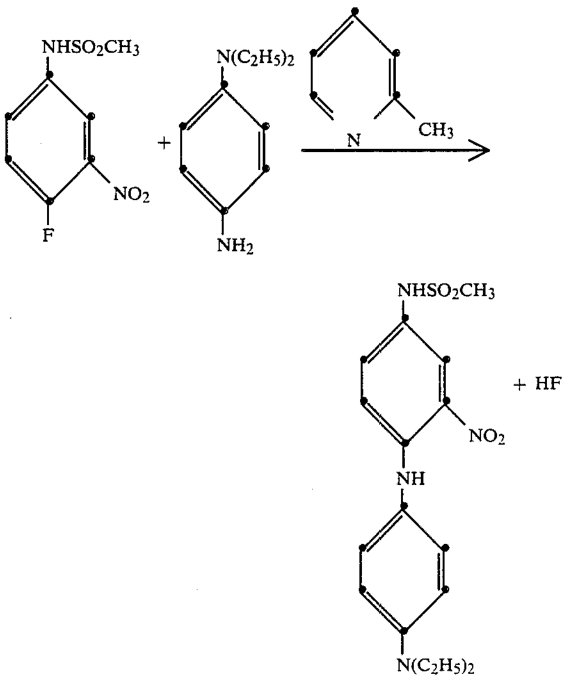

A solution of the nitro compound and the p-phenylenediamine compound in α-picoline are refluxed overnight under nitrogen. The mixture is the poured over ice, and after the ice has melted the composition is filtered. The collected solid is washed with water until clear washings are obtained and air-dried. The desired intermediate is recrystallized from a suitable solvent such as ethyl acetate to provide the desired solid having a melting point of 168° C. to 170° C. This intermediate was identified by elemental analysis.

Then the following reaction is carried out:

-continued
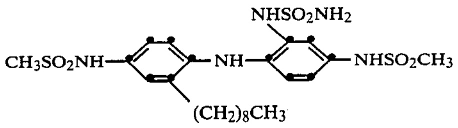
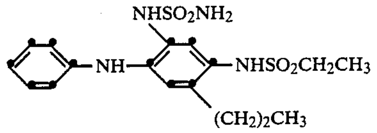
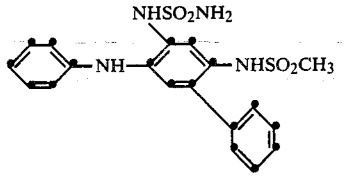
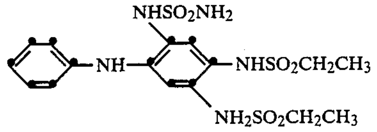
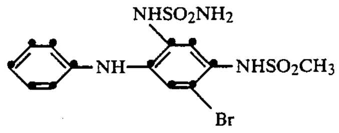
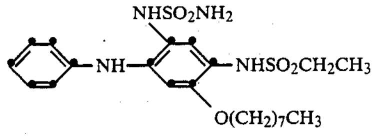
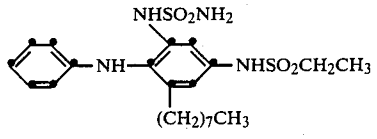
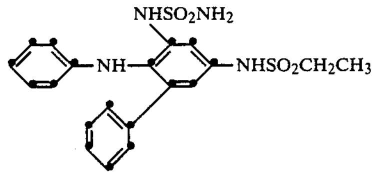
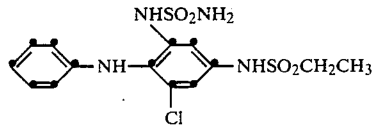
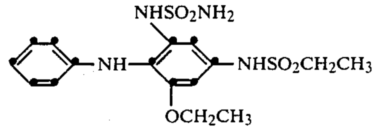
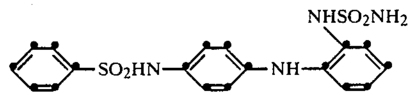
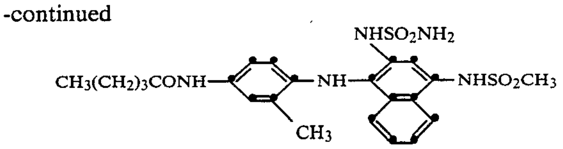
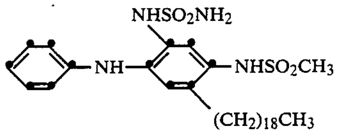
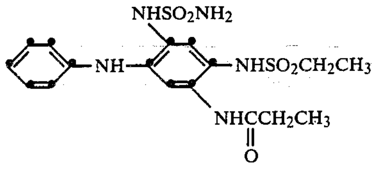
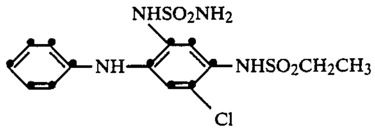
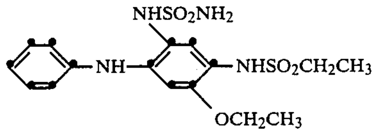
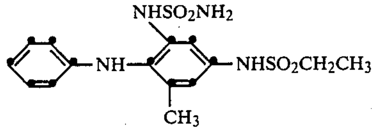
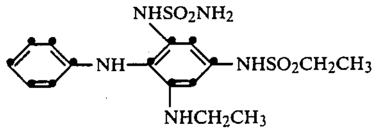
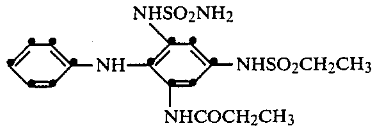
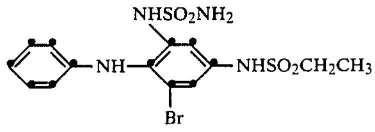
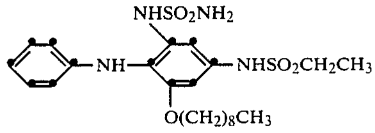
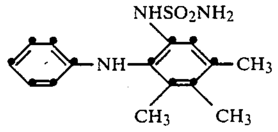

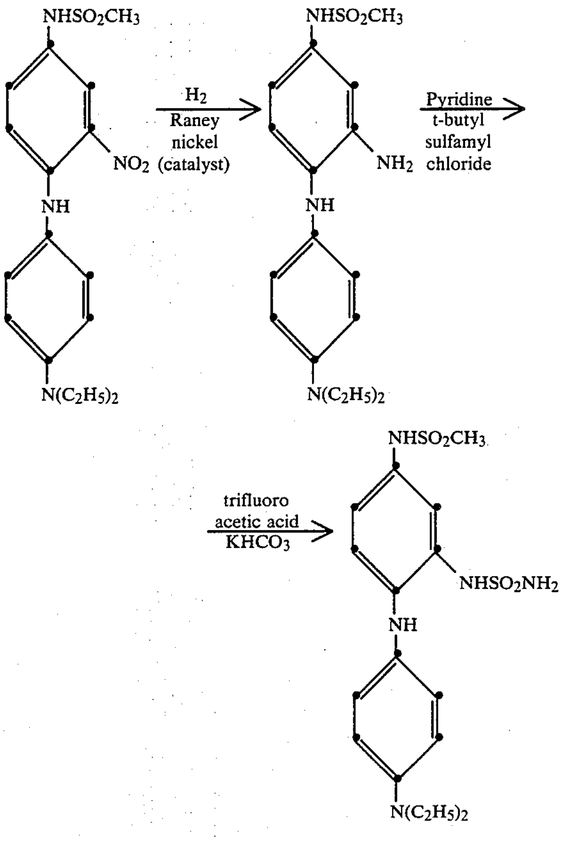

A solution of the described nitro-substituted sulfonamidodiphenylamine in degassed tetrahydrofuran is reduced over Raney nickel (catalyst) at room temperature (about 20° C.) at 40 psi of hydrogen. The catalyst is removed by filtration and the filtrate concentrated to dryness under nitrogen to protect the reaction mixture against air oxidation. A dark blue gum is obtained. This desired product is dissolved in pyridine, cooled to 0°–5° C. The resulting composition is stirred and tertiarybutylsulfamyl chloride is added proportionwise. Following removal of the pyridine under vacuum the residue is taken up in a suitable solvent such as ethyl acetate and ice water. The desired product is then separated and purified to provide a compound having a melting point of 158° C. to 160° C. The desired product is identified by mass spectrographic analysis and nuclear magnetic resonance analysis, as well as elemental analysis. Three grams of this compound are added to 25 ml of trifluoroacetic acid at 5° C. under nitrogen and allowed to come to room temperature (about 20° C.) over a four hour period. Stirring is continued overnight to provide a complete reaction. The mixture is then poured into ice water/ethyl acetate and stirred with potassium bicarbonate. The ethyl acetate layer is then washed with saturated aqueous sodium bicarbonate, washed three times with water and dried. The resulting product has a melting point of 178° C. The product is identified by thin layer chromatographic (TLC) analysis, nuclear magnetic resonance analysis, and elemental analysis.

A corresponding phenazine dye is produced from the diphenylamine compound according to the invention by intramolecular reaction following oxidation by an oxidizing agent. This is effected by means of a suitable oxidizing agent, as described, including, for example an oxidized crossoxidizing developing agent, a ferricyanide, fatty acid silver salt, dichromate, oxygen, or permanganate oxidizing agent. This reaction is illustrated as follows:

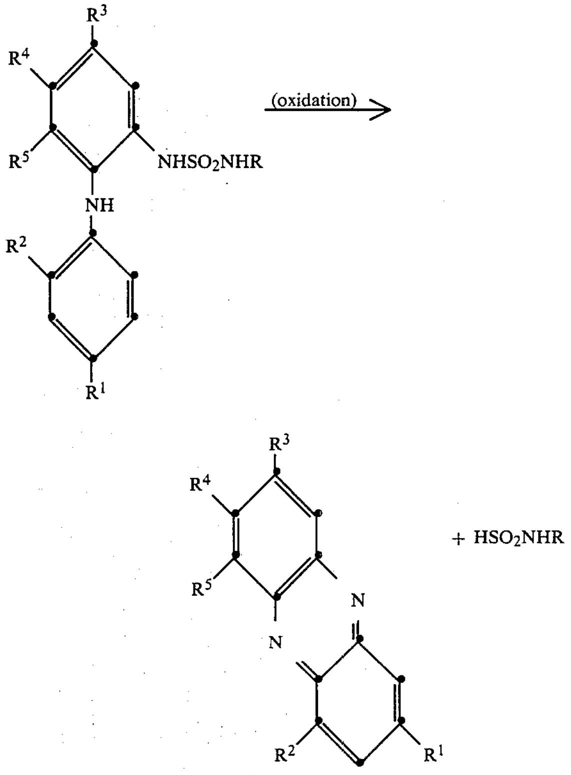

$$HSO_2NHR \xrightarrow{(heat)} SO_2 + H_2NR$$

wherein R, $R^1$, $R^2$, $R^3$, $R^4$ and $R^5$ are as defined. The sulfonylamine fragment released from the diphenylamine compound thermally decomposes to provide ammonia or an amine and $SO_2$.

The hue of the phenazine dye produced from the diphenylamine compound varies, depending upon such factors as the particular groups on the diphenylamine, processing conditions, and other components in the photographic material. In some cases the phenazine dye from the diphenylamine is not visible in the visible region of the electromagnetic spectrum. For example, some phenazine dyes absorb in the ultraviolet region of the electromagnetic spectrum, such as the phenazine dye of following Example 20. Most phenazine dyes produced from the diphenylamine compounds are visible in the visible region of the electromagnetic spectrum. The nature of absorption and degree of absorption of the phenazine dyes depends on the nature of the substituent groups on the phenazine nucleus.

Most of the diphenylamines in a photographic material according to the invention absorb electromagnetic radiation outside the visible region of the electromagnetic spectrum before imagewise exposure and processing of the photographic material. The nature of the absorption and degree of absorption of the diphenylamine compound depend upon the nature of the substituent groups on the diphenylamine.

The term "colorless" herein means that the diphenylamine compound according to the invention does not absorb radiation to an undesired degree in the visible region of the electromagnetic spectrum. In some photographic materials, the diphenylamine compound absorbs radiation in certain areas of the electromagnetic spectrum which does not adversely affect the desired properties of the photographic material or the desired image formed upon processing.

Generally, the diphenylamine compound is colorless in a photographic material prior to processing. Some of the diphenylamines have a slight yellow color in the photographic material. This slight color is not considered unacceptable.

The photographic materials according to the invention comprise a photographic component, preferably a photographic silver salt such as photographic silver halide. It is essential that the photographic component not adversely affect the desired imaging process, such as the intramolecular reaction that occurs in the photographic material. Examples of useful photographic silver halides are silver chloride, silver bromide, silver bromoiodide, silver chlorobromoiodide, silver iodide and mixtures thereof. The photographic silver halide is generally present in the photographic material in the form of an emulsion which is a dispersion of the photographic silver halide and a suitable binder. The photographic silver halide is present in a range of grain sizes from fine grain to coarse grain. The composition containing the photographic silver halide is prepared by any of the well known procedures in the photographic art, such as described in *Research Disclosure,* December, 1978, Item No. 17643. The photographic silver halide material contains addenda commonly present in photographic silver halide materials, such as chemical sensitizers, brighteners, antifoggants, emulsion stabilizers, light absorbing or scattering materials, hardeners, coating aids, plasticizers, lubricants and antistatic materials, matting agents, development modifiers and other addenda described in *Research Disclosure,* December, 1978, Item No. 17643. The photographic silver halide can comprise, for example, internal image photographic silver halide and internally sensitized covered grain silver halide to produce positive images.

The photographic silver halide is generally spectrally sensitized by means of spectral sensitizing dyes, as described in *Research Disclosure,* December, 1978, Item No. 17643. Spectral sensitizing dyes which are useful in the photographic materials of the invention include polymethine sensitizing dyes which include the cyanines, merocyanines, complex cyanines and merocyanines (including tri-, tetra- and polynuclear cyanines and merocyanines), as well as oxonols, hemioxonols, styryls, merostyryls and streptocyanines. Combinations of spectral sensitizing dyes are useful.

The photographic material contains a range of concentrations of photographic silver halide. An optimum concentration of photographic silver halide will depend upon such factors as the desired image, processing conditions, particular diphenylamine compound according to the invention and other components in the photographic material. A useful concentration of photographic silver halide in the photographic material according to the invention is within the range of about 1 mole to about 10 moles of photographic silver halide per mole of diphenylamine compound according to the invention in the photographic material. The coverage of photographic silver halide is generally less than otherwise might be useful, due to the enhancing properties of the phenazine dye produced upon processing of the photographic material.

The diphenylamine compound according to the invention is in any suitable location in the photographic material which produces the desired phenazine dye and the desired sulfonylamine fragment upon processing. According to the invention, the diphenylamine compound is in a location with respect to the photographic silver halide that produces a silver image and releases a sulfonylamine fragment upon appropriate processing. If desired, a portion of the diphenylamine compound is in a layer contiguous to the layer of the photographic element comprising photographic silver halide. The term "in reactive association" herein means that the photographic silver halide and the diphenylamine compound are in a location with respect to each other which enables the desired photographic material upon processing to produce a desired image.

Many optional developing agents are useful for aiding in developing an image in a photographic material according to the invention. Silver halide developing compositions are optionally useful according to the invention. Such an optional developing agent is a crossoxidizing developing agent which becomes oxidized during development by aiding in reducing exposed silver halide to silver metal. The oxidized developer then aides in crossoxidizing the diphenylamine comound to form the desired phenazine dye and release the sulfonylamine fragment.

A crossoxidizing developing agent (COD) helps the diphenylamine to be oxidized. The crossoxidizing developing agent is alternatively viewed as an electron transfer agent which shuttles electrons between the developing silver halide and the diphenylamine.

The requirements for a crossoxidizing developing agent in the most general cases are:

(a) the developing agent must have sufficient electrochemical potential under the conditions of use to develop exposed silver halide;

(b) in its oxidized form, the developing agent must be of such electrochemical potential as to oxidize the diphenylamine; and (c) in its oxidized form the developing agent must be stable to decomposition by other chemical reaction for a sufficient time to undergo the redox reaction with the diphenylamine.

If one or more of these conditions is not met, the developing agent is not a crossoxidizing developing agent. Whether a particular developing agent meets the requirements of a crossoxidizing developing agent depends upon the conditions under which development occurrs, other components in the developing composition, pH of the developing composition, the temperature of development, and the length of development time. Developing agents which meet the requirements of a crossoxidizing developing agent under development conditions are useful. Especially useful examples of developing agents that are crossoxidizing developing agents are 3-pyrazolidone developing agents, such as 1-phenyl-3-pyrazolidone, 1-phenyl-4,4-dimethyl-3-pyrazolidone and 4-hydroxymethyl-4-methyl-1-phenyl-3-pyrazolidone. Such crossoxidizing developing agents are described in, for example, U.S. Pat. No. 3,938,995. Combinations of developing agents are also useful. Combinations of non-crossoxidizing developing agents and cross oxidizing developing agents are useful provided that desired photographic properties are not adducible cobalt(III) complex containing releasable amine ligands.

A preferred embodiment of the invention comprises a photographic element comprising a support having thereon in reactive association in binder photographic silver halide and a dye precursor comprising a diphenylamine containing, in an ortho position to the amine of the diphenylamine, a sulfonyldiamido group that is capable upon oxidation of the diphenylamine of releasing a sulfonylamine fragment which, in turn, is capable of thermally releasing ammonia or an amine; and, also comprising, in at least one operatively associated layer, an amine activatable image precursor composition comprising at least one cobalt(III) complex having releasable ligands and an image forming material which generates an image in response to the release of the ligands. A preferred image precursor composition comprising at least one cobalt(III) complex comprises a cobalt(III) hexammine complex and ortho-phthalaldehyde. Such cobalt(III) complex image forming materials are known in the imaging art and are described in, for example, *Research Disclosure* Item No. 16845; *Research Disclosure* Item No. 12617; *Research Disclosure* Item No. 18535; *Research Disclosure* Item No. 15874; *Research Disclosure* Item No. 18436; U.S. Pat. No. 4,273,860; U.K. published application No. 2,012,445A; European Pat. No. 12,855; and published application WO 80/01322, the disclosures of which are incorporated herein by reference.

Preferred cobalt(III) complexes useful in an imaging element according to the invention feature a molecule having a cobalt atom or ion surrounded by a group of atoms, ions or other molecules which are generically referred to as ligands. The cobalt atom or ion in the center of these complexes is a Lewis acid while the ligands are Lewis bases. Trivalent cobalt complexes, that is cobalt(III) complexes, are generally most useful according to the invention because the ligands are relatively tenaciously held in these complexes and released when the cobalt is reduced to the (II) state.

Preferred cobalt(III) complexes are those having a coordination number of six. A wide variety of ligands are useful to form a cobalt(III) complex. The preferred cobalt(III) complex is one which aids in generating an amine to generate a dye or destroy a dye. Cobalt(III) complexes which rely upon chelation of cobalt(II) to form added dye density are also useful in photographic materials according to the invention. Useful amine ligands in cobalt(III) complexes according to the invention include, for example, methylamine, ethylamine, ammines, and amino acids such as glycinato. The term "ammine" refers to ammonia, when functioning as a ligand, whereas "amine" indicates the broader class noted above. The ammine complexes are highly useful in producing dye images.

The cobalt(III) complexes useful according to the invention include neutral compounds which are entirely free of either anions or cations. The cobalt(III) complexes also include one or more cations and anions as determined by the charge neutralization rule. Herein the terms "anion" and "cation" refer to non-ligand anions and non-ligand cations unless otherwise indicated. Useful cations are those which produce readily soluble cobalt(III) complexes, such as alkaline metals and quaternary ammonium cations.

A wide variety of anions are useful, such as those listed in *Research Disclosure,* Item No. 18436. The choice of an optimum anion depends in part on whether or not added compounds are present that are sensitive to, or reactive with, the anion.

The image forming material containing a cobalt(III) complex optionally comprises compounds or compositions in addition to the cobalt(III) complex. Such materials are, for example, dye forming materials or dyes which are bleachable in response to ammonia or amines. Examples of dye forming materials which also comprise destabilizer materials to interact with the cobalt(III) complex are known in the photographic art such as described in U.S. Pat. No. 4,273,860 which is incorporated herein by reference. Such dye forming materials include, for example, 4-methoxynaphthol which forms a blue dye when oxidized and protonated diamine destabilizer material which when associated with a conventional color coupler will form a dye when it is oxidized by the reduction of the cobalt(III) complex. Examples of image forming materials useful in addition to a destabilizer material include phthalaldehyde, also present as an amplifier; an ammonia-bleachable or color alterable dye such as a cyanine dye, styryl dye, rhodamine dye, azo dye or pyrlium dye; a dye precursor such as a ninhydrin; or a diazo coupler material which is capable of forming a diazo dye. Details of these examples are described in, for example, *Research Disclosure,* October 1974, Item 12617, the disclosure of which is incorporated herein by reference. Another optional addenda is a compound which will chelate with the cobalt(II) to form a dye.

When ammonia-bleachable image forming materials are present in the photographic element according to the invention the ammonia-bleachable materials are preferably in a layer separate from the ammonia producing components of the material.

The layer comprising cobalt(III) complexes preferably comprises a binder. Useful binders are described in, for example, *Research Disclosure,* October, 1974, Item No. 12617, the description of which is incorporated herein by reference. Generally useful binders are acetates, cellulose compounds, vinyl polymers, polyacrylates and polyesters. In addition, it is preferred that the binder be selected which will maximize the preferred hue and density of dye produced upon exposure and development. Preferred examples of such binders include polysulfonamides, for example, poly(ethylene-co-1,4-cyclohexylenedimethylene-1-methyl-2,4-benzenedisulfonamide), poly(ethylene-co-hexamethylene-1-methyl-2,4-benzenedisulfonamide) and poly(methacrylonitrile).

A preferred amine responsive element according to the invention comprises a support having thereon a layer comprising, in a sulfonamide binder, phthalaldehyde and a hexamine cobalt(III) trifluoroacetate which is overcoated with a suitable polymeric overcoat such as a poly(acrylamide-co-N-vinyl-2-pyrrolidone-co-2-acetoacetoxyethylmethacrylate). Such an imaging element when placed contiguous to a photographic element containing photographic silver halide and a diphenylamine compound according to the invention produces a dye image upon heating the combined layers during processing.

A photographic element according to the invention is preferably a photothermographic material such as a photothermographic silver halide material. Photothermographic materials in which the diphenylamine compounds are useful are described in, for example, *Research Disclosure,* June 1978, Item No. 17029, which is incorporated herein by reference. For example, a dye versely affected. Selection of an optimum silver halide developing agent or developing agent combination depends upon such factors as the desired image, the particular photosensitive silver halide, processing conditions, particular diphenylamine compound, pH of the developing composition, the temperature of the development process and the length of development time.

The silver halide developing agent or developing agent combination is optionally incorporated in the photographic material. Generally, the developing agent is most useful incorporated in the photographic material.

The optional crossoxidizing developing agent is useful in a range of concentrations in the photographic material or in a processing composition in which the photographic material is processed. A useful concentration of optional crossoxidizing developing agent when the crossoxidizing developing agent is present in the photographic material is within the range of about 0.1 to about 1.0 mole of developing agent per mole of diphenylamine in the photographic material. A useful concentration of optional developing agent in the processing solution for processing a photographic material containing a diphenylamine according to the invention is within the range of about 0.5 to about 2 grams of developing agent per liter of processing solution.

The term "developing agent" herein includes compounds which are developing agents and developing agent precursors. That is, those compounds are included which are not developing agents in the photographic material until a condition occurs, such as contact with a suitable activator for the photographic material.

The tone of the image, such as the silver image and dye image, produced in a photographic material according to the invention varies depending upon such factors as the silver morphology of the developed silver image, the covering power of the silver materials, the particular phenazine dye formed, processing conditions, concentration of components, and other materials present during imaging. In photographic materials that provide a brown silver image, a phenazine dye produced from the diphenylamine compound is especially useful which is complementary in hue to the silver image.

The photographic materials according to the invention generally comprise a binder. Binders are useful alone or in combination in a photographic material according to the invention. Useful binders in the photographic silver halide material include both naturally occurring substances such as proteins, for example, gelatin, gelatin derivatives, cellulose derivatives, polysaccharides such as dextran, gum arabic and the like; and synthetic polymeric materials which are compatible with the diphenylamine compound, such as water soluble polyvinyl compounds like polyvinylpyrrolidone and acrylamide polymers.

If desired, the photographic elements according to the invention contain an overcoat layer and/or interlayer and/or subbing layer to provide desired properties. The overcoat layer, for example, increases resistance to abrasion and other markings on the element. The overcoat layer, interlayer or subbing layer contain, alone or in combination, vehicles and binders that are useful in the layer of the element containing the photosensitive silver halide. Gelatin is an especially useful binder.

A photographic element according to the invention comprises a variety of supports. Useful supports include those which are resistant to adverse changes in structure due to processing conditions and which do not adversely affect the desired sensitometric properties of the photographic materials. Useful supports include, for example, cellulose ester, poly(vinyl acetal), poly(ethylene terephthalate) and polycarbonate films, as well as related films and resinous materials. Glass, paper, metal and the like supports are also useful. A flexible support is generally most useful.

In preparing a photographic material comprising the diphenylamine according to the invention, a dispersion solvent is optionally useful to produce a coating composition. A coupler solvent known in the photographic art is optionally useful for aiding dispersion of the diphenylamine dye precursor. Examples of optional coupler solvents include N-n-butylacetanilide, diethyl lauramide, di-n-butylphthalate and 2,4-ditertiaryamylphenol. The diphenylamine compound is also optionally loaded into a latex, or a non-solvent dispersion is prepared if desired.

The photographic materials according to the invention are coated on a suitable support by procedures known in the photographic art. Such procedures include, for example, immersion or dip coating, roller coating, reverse roll coating, air knife coating, doctor blade coating, spray coating, extrusion coating, dip coating, stretch flow coating and curtain coating.

The photographic materials according to the invention are generally imagewise exposed by means of various forms of energy to produce a developable image. Such forms of energy include those to which the photographic material, especially the photographic silver halide, is sensitive. These forms of energy encompass the ultraviolet, visible and infrared regions of the electromagnetic spectrum, as well as electron beam and beta radiation, gamma ray, x-ray, alpha particle, neutron radiation and other forms of corpuscular wavelike radiant energy in either non-coherent (random phase) forms or coherent (in phase) forms as produced by lasers. Exposures are monochromatic, orthochromatic or panchromatic, depending upon the spectral sensitization of the photographic component, especially the photographic silver halide. Imagewise exposure is generally for a sufficient time and intensity to produce a developable latent image in the photographic material.

The described photographic materials according to the invention are processed in a process which produces a silver image and dye image in the photographic element. The photographic silver halide contained in the photographic element according to the invention is optionally processed following exposure by associating the silver halide with an aqueous alkaline medium in the presence of a suitable crossoxidizing developing agent contained in the medium or the element according to the invention.

The photographic material according to the invention preferably comprises at least one image forming material which generates an image in response to the presence of ammonia or an amine from the sulfonylamine fragment released from the diphenylamine compound. An illustrative preferable example of such an amine responsive material is one that comprises an aromatic dialdehyde capable of reacting with ammonia or an amine generated from the sulfonylamine fragment. Such an aromatic dialdehyde is, for example, orthophthalaldehyde capable of reacting with ammonia or an amine generated from the sulfonylamine fragment. The photographic material also preferably comprises a reimage or dye and silver image is produced in a photothermographic material comprising, in binder, in reactive association, (a) photographic silver halide and
(b) a diphenylamine compound according to the invention.

The photothermographic material optionally comprises a crossoxidizing photographic silver halide developing agent. The photothermographic material also optionally comprises an auxiliary base release agent, such as a base release agent described in *Research Disclosure* Item No. 17029.

The photothermographic material is generally imagewise exposed to light to provide a developable latent image which is then developed by merely uniformly heating the photothermographic material to processing temperature, such as a temperature within the range of about 100° C. to about 200° C. This enables formation of a phenazine dye, a silver image and release of the sulfonylamine fragment which is thermally decomposed to form ammonia or an amine which aids in processing and formation of a dye. The ammonia or amine released is generally transferred to a contiguous layer containing an amine or ammonia responsive imaging material.

Another form of photothermographic material according to the invention comprises, in binder, in reactive association, (a) photographic silver halide which is formed in situ or ex situ,
(b) an organic metal salt oxidizing agent, such as an organic silver salt oxidizing agent, and
(c) a diphenylamine compound according to the invention.

The photothermographic material also optionally comprises an organic crossoxidizing reducing agent for the organic metal salt oxidizing agent, such as a 3-pyrazolidone reducing agent. This photothermographic material is imagewise exposed to light and then uniformly heated to provide a desired image, generally a silver image and a dye image.

A variety of organic silver salt oxidizing agents are useful in a photothermographic material according to the invention. Examples of useful organic silver salt oxidizing agents are described in, for example, *Research Disclosure,* June 1978, Item No. 17029, the description of which is incorporated herein by reference. Examples of useful organic silver salt oxidizing agents include silver behenate, silver palmitate, silver stearate as described in, for instance, *Research Disclosure* Item No. 17029, and, for instance, silver salts of 1,2,4-mercaptotriazole derivatives such as described in *Research Disclosure,* June 1977, Item No. 15869, which are incorporated herein by reference. Another useful class of organic silver salt oxidizing agent is represented by complexes or salts of silver with a nitrogen acid, such as a nitrogen acid selected from the group consisting of imidazole, pyrazole, urazole, 1,2,4-triazole and 1H-tetrazole nitrogen acids or combinations of these acids. These silver salts of nitrogen acids are described in, for example, *Research Disclosure,* October 1976, Item No. 15026, the disclosure of which is incorporated herein by reference. Examples of useful silver salts or complexes of nitrogen acids include silver salts or complexes of 1H-tetrazole; dodecyltetrazole; 5-n-butyl-1H-tetrazole; 1,2,4-triazole; urazole; pyrazole; imidazole; and benzimidazole. A further class of useful organic silver salt oxidizing agents includes silver salts of certain heterocyclic ion compounds such as described in U.S. Pat. No. 3,893,860, the description of which is incorporated herein by reference. Selection of an optimum organic silver salt or complex oxidizing agent, or combination of such oxidizing agents, will depend upon such factors as the desired image, particular silver halide, processing temperature and other conditions, and particular diphenylamine compound according to the invention.

The terms "salt" and "complex" herein include any type of bonding or complexing mechanism which enables the resulting material to provide desired imaging properties in the photographic materials according to the invention. In some instances the exact bonding of the described organic silver salt or complex is not fully understood. The terms "salt" and "complex" are intended to include neutral complexes and non-neutral complexes.

A preferred photothermographic element according to the invention comprises on a support, in a poly(vinylbutyral) binder, in reactive association, (a) photographic silver halide,
(b) a silver dodecyltetrazolate oxidizing agent,
(c) a toner, and
(d) a dye precursor consisting essentially of a compound selected from the group consisting of described compounds (A), (B), (C), (D) and (E) and combinations thereof.

Such a photothermographic element can also comprise a contiguous layer containing an amine responsive imaging material, such as a combination of orthophthalaldehyde and a cobalt(III) amine complex which forms a dye in response to the ammonia or amine released from the layer comprising the diphenylamine dye precursor upon heating the photothermographic element after exposure. The photothermographic element also optionally comprises an auxiliary silver halide developing agent such as a 3-pyrazolidone silver halide developing agent.

A process of developing an image in an exposed photothermographic element according to the invention comprises heating the element, preferably uniformly, to a temperature within the range of about 100° C. to about 180° C. until the image is developed. During this heating step ammonia or an amine is released from the sulfonylamine fragment from the diphenylamine dye precursor. The ammonia or amine is useful for aiding development of an image or in imaging by means of an amine responsive imaging material. Development of an image in a contiguous cobalt(III) complex containing layer also in carried out at a temperature within the range of about 100° C. to about 180° C. until the image in the cobalt(III) complex containing layer is developed.

Heating of a photothermographic element according to the invention is carried out until a desired image is developed, typically within about 2 to about 60 seconds. Selection of an optimum time and temperature will depend upon such factors as the desired image, particular components of the photothermographic material, the particular amine responsive imaging component, the particular diphenylamine compound and other components in the photothermographic material.

A variety of means are useful to produce the necessary heating of the photothermographic material to develop the desired image. The heating means is, for example, a suitable hot plate, heated drum, iron, or roller, infrared heating means, hot air heating means or the like.

Processing according to the invention is generally carried out under ambient conditions of pressure and humidity. Pressures and humidity outside normal atmospheric conditions are useful if desired; however, atmospheric conditions are preferred.

In photothermographic silver halide elements according to the invention it is generally desirable to have a stabilizer or stabilizer precursor in the photothermographic material to provide improved post processing image stability. It is desirable in most instances to stabilize the silver halide after processing in order to avoid post processing printup. A variety of stabilizers and stabilizer precursors are useful in the photographic materials according to the invention. The stabilizers and stabilizer precursors are useful alone or in combination. Generally useful stabilizers and stabilizer precursors are sulfur compounds that form a stable silver mercaptide after image development with the photosensitive silver material at processing temperatures. Photolytically active halogenated organic compounds are also useful in some photothermographic materials according to the invention. Such stabilizers and stabilizer precursors are described in, for example, *Research Disclosure,* June 1978, Item No. 17029, the description of which is incorporated herein by reference. Selection of an optimum stabilizer or stabilizer precursor or combination thereof will depend upon such factors as the particular photosensitive silver halide, processing conditions, desired image, particular diphenylamine compound and other components in the photothermographic material.

The photothermographic material according to the invention generally comprises an image toner to produce a more nearly neutral appearing or black tone image upon processing. Combinations of image toners are also useful. The optimum toning agent or toning agent combination will depend upon such factors as the particular silver halide, the desired image, particular processing conditions, particular diphenylamine compound and other components in the photothermographic material. In a photothermographic material comprising an organic silver salt oxidizing agent which is a silver salt of a nitrogen acid useful toning agents include, for example, 5-amino-1,3,4-thiadiazole-2-thiole; 3-mercapto-1,2,4-triazole and bis(dimethylcarbamyl)disulfide. Other toning agents are described in, for example, *Research Disclosure,* June 1978, Item No. 17029, the description of which is incorporated herein by reference. The toning agent is useful in a range of concentrations in a photothermographic material according to the invention. The optimum concentration of toning agent or toning agent combination will depend upon the described factors such as the particular photosensitive silver halide, particular desired image, processing conditions, particular diphenylamine compound and other components in the photothermographic material. A preferred concentration of toning agent is within the range of about 0.01 to about 0.1 mole of toning agent per mole of organic silver salt oxidizing agent in the photothermographic material.

The photothermographic material generally comprises a melt forming compound to aid in processing. The melt forming compound generally provides an improved developed image. The term "melt forming compound" herein means a compound which upon heating to the described processing temperature produces an improved reaction medium, generally a melt medium, within which the image-forming combination and photosensitive component produce better image development. The exact nature of the reaction medium in the photothermographic material at processing temperatures is not fully understood; however, it is believed at the reaction temperatures a melt occurs which permits the reaction components to better interact and diffuse into contiguous layers of the photothermographic element. Useful melt forming compounds are generally components separate from the image forming combination, although the image forming combination and other addenda in the photothermographic material enter into the melt formation. Generally useful melt forming compounds are amides, imides, cyclic ureas and triazoles which are compatible with other components of the photothermographic materials. Useful melt forming compounds are generally selected from those described in, for example, U.S. Pat. No. 3,438,776. Examples of useful melt forming compounds include acetamide, 1,3-dimethylurea, N-propylurea, 2-pyrrolidone and formamide.

The melt forming compound is useful in a range of concentrations in the photothermographic materials according to the invention. Preferred concentrations of melt forming compound are within the range of about 0.5 to about 2 parts by weight of melt forming compound per gram of organic silver salt oxidizing agent in the photothermographic material. The optimum concentration of melt forming compound will depend upon the described factors.

The diphenylamine compound is, in one embodiment of the invention, incorporated in a photographic silver halide processing composition for producing a silver image and dye image. Such a processing composition optionally comprises a cross-oxidizing photographic silver halide developing agent and the desired diphenylamine compound or a combination of such compounds. The photographic processing composition is, for example, a silver halide developing composition, hardening composition or stabilizing composition. The processing composition generally comprises an auxiliary base or base release agent. An example of a useful photographic silver halide processing composition comprises a 3-pyrazolidone crossoxidizing photographic silver halide developing agent and a diphenylamine compound comprising:

1. N-t-butyl-N'-[2-(4-methanesulfonamidoanilino)-5-chlorophenyl]sulfamide;
2. N-t-butyl-N'-[2-(4-N,N-diethylaminoanilino)-5-chlorophenyl]sulfamide;
3. N-t-butyl-N'-[2-(4-N,N-diethylaminoanilino)-5-methanesulfonamidophenyl]sulfamide;
4. N-[(4-N,N-diethylaminoanilino)-5-methanesulfonamidophenyl]sulfamide;
5. N-[(4-N,N-methoxyanilino)-5-methanesulfonamidophenyl]sulfamide;
6. N-[(4-N,N-methylaminoanilino)-5-methanesulfonamidophenyl]sulfamide;

or combinations of such sulfamide compounds.

The following examples are included for a further understanding of the invention.

EXAMPLE 1

This relates to preparation of the compound:

forming component. The product was also identified by nuclear magnetic resonance analysis and elemental analysis.

EXAMPLE 6

This relates to preparation of the compound:

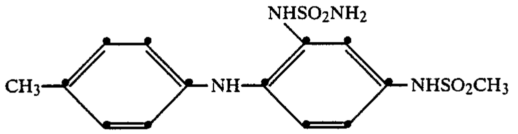

Three grams of 4-methyl-2'-N-(t-butylsulfamyl-)amino-4'-methanesulfonamidodiphenylamine were added portionwise, with stirring, to 25 milliliters of trifluoroacetic acid at 10° C. After stirring overnight at room temperature (about 20° C.), the mixture was concentrated by aspiration and the residue taken up with ethyl acetate and an ice bath of aqueous sodium bicarbonate. The ethyl acetate extract was washed with saturated aqueous sodium bicarbonate 2 times and with water 3 times, then dried and concentrated. A small portion of n-pentane was added and recrystallization of the product yielded 1.0 grams of light pink solids having a melting point of 163°–164° C. The desired product was identified by thin layer chromatographic analysis showing one major pinkish-orange dye forming component. The product was also identified by nuclear magnetic resonance analysis and elemental analysis.

The following diphenylamine compounds were prepared by procedures similar to those described in Examples 1 and 2:

TABLE II

Representative Compounds Comprising a Sulfonyldiamido Group

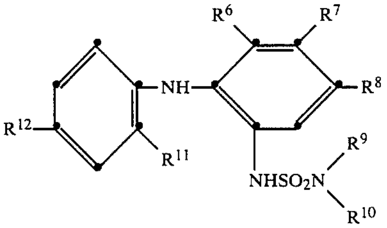

| Examples | $R^{12}$ | $R^8$ | $R^9$ | $R^{10}$ | $R^{11}$ | $R^6$ | $R^7$ | Melting Point |
|---|---|---|---|---|---|---|---|---|
| 7 | *$Et_2N-$ | $-NHSO_2CH_3$ | H | H | H | H | H | glass |
| 8 | $CH_3$ | $-NHSO_2CH_3$ | H | H | H | H | H | 163–164° C. |
| 9 | $CH_3O-$ | $-NHSO_2CH_3$ | H | H | H | H | H | 138–140° C. |
| 10 | $CH_3SO_2NH-$ | —Cl | H | H | H | H | H | 98–103° C. |
| 11 | O<br>‖<br>$C_4H_9NHCONH-$ | —Cl | H | H | H | H | H | 174–175.5° C. |
| 12 | O<br>‖<br>$C_7H_{15}CNH-$ | —Cl | H | H | H | H | H | 177–178° C. |
| 13 | $Et_2N-$ | $-NHSO_2CH_3$ | $-CH_3$ | $-CH_3$ | H | H | H | 154–156° C. |
| 14 | $CH_3SO_2NH-$ | $-OCH_3$ | H | H | H | H | H | glass |
| 15 | $CH_3SO_2NH-$ | —Cl | H | $-CH_3$ | H | H | H | glass |
| 16 | $Et_2N-$ | H | H | H | H | H | H | 135–136° C. |
| 17 | $Et_2N-$ | $-NHSO_2CH_3$ | H | H | $-CH_3$ | H | H | 180–181° C. |

*Et herein means ethyl

EXAMPLE 18

Photothermographic Material and Process Comprising Color-forming Compound According to the Invention A photothermographic element was prepared by mixing the following components and coating them on a subbed poly(ethylene terephthalate) film support at a wet coating thickness of 8 mils (203.2 microns).

| Component | Concentration in Grams |
|---|---|
| Acetone | 0.6 |
| 1-phenyl-3-pyrazolidone | 0.020 |
| Poly(vinylbutyral) (binder) (10% by weight in toluene) (BUTVAR B-76, a trademark of and available from the Monsanto Company, U.S.A.) | 0.4 |
| Silver dodecyltetrazolate dispersion (prepared as described in U.S. Pat. No. 4,220,709) | 1.0 |
| Silver bromoiodide poly(vinylbutyral) emulsion* | 0.14 |
| Diphenylamine (color-forming compound): 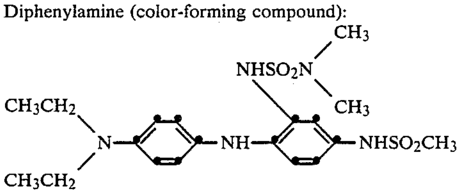 | 0.035 |
| 5-Amino-1,3,4-thiadiazole-2-thiol (toner) | 0.00025 |

*The silver bromoiodide poly(vinylbutyral) emulsion was prepared by mixing anhydrous lithium iodide, anhydrous lithium bromide and silver trifluoroacetate in an acetone solution comprising poly(vinylbutyral) as a peptizer.

The resulting emulsion contained 15.7% solids and 40 grams of silver per liter of solution.

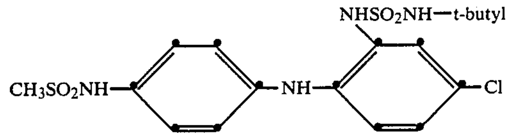

Three grams (0.0087 mole) of 4-N-methanesulfonamido-2'-nitro-4'-chlorodiphenylamine were added to 100 milliliters of dry tetrahydrofuran and reduced over Raney nickel (catalyst) on Parr apparatus overnight at 39 pounds/inch$^2$ hydrogen pressure. The 2'-amino derivative was isolated and dissolved in 15 milliliters of dry pyridine. After cooling to 5° C., 1.7 grams of N-t-butylsulfamylchloride were added and the resulting mixture stirred for 4 hours at room temperature (about 20° C.). After standing for 3 days at room temperature (about 20° C.), a tan glassy product, weighing about 4 grams was isolated. The product was recrystallized from ethylacetate and dichloromethane at 5° C. resulting in 2 to 4 grams of pink solids melting at 146°-148° C. The product was identified by thin layer chromatographic analysis that yielded a blue dye upon oxidation. The product was also identified by nuclear magnetic resonance analysis and elemental analysis.

EXAMPLE 2

This relates to preparation of the compound:

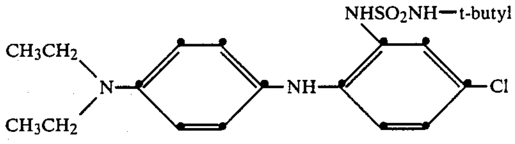

3.19 grams (0.01 mole) of 4-N,N-diethyl-amino-2'-nitro-4'-chlorodiphenylamine were added to 100 milliliters of tetrahydrofuran and reduced with hydrogen over Raney nickel (catalyst) on a Parr apparatus overnight. The residue following fitration was dissolved in 15 milliliters of dry pyridine, chilled to about 5° C. and the resulting composition stirred until further reaction ceased. The desired product was isolated and contained a purplish dye forming material with a minor impurity. The product was recrystallized from 20:80 parts by volume ethylacetate:hexane at 5° C. to provide 2 grams of light pink solids having a melting point of 121°-122° C. The desired product was identified by nuclear magnetic resonance analysis and elemental analysis.

EXAMPLE 3

This relates to preparation of the compound:

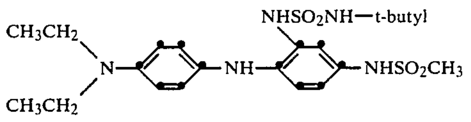

7.06 grams of 4-N,N-diethylamino-2'-nitro-4'-methanesulfonamidodiphenylamine were reduced to the 2'-amino derivative as described in preparations in Examples 1 and 2. The resulting blue gum was dissolved in 30 milliliters of dry pyridine, cooled to 0°-5° C. and then with stirring 3.5 grams (0.02 mole) of t-butylsulfamylchloride were added portionwise. Following removal of the pyridine under vacuum, the residue was taken up with ethyl acetate and ice water. The ethyl acetate layer was washed 3 times with water, dried, and concentrated until tan solids appeared. These solids were diluted with ligroin and the solids recollected. After drying under vacuum, the solids were recrystallized from 60:40 parts by volume ethylacetate:acetone at 5° C. and dried. Light pink solids weighing 4.0 grams having a melting point of 158°-160° C. resulted. The desired product was identified by thin layer chromatographic analysis to provide one major cyan dye forming component. The product was also identified by nuclear magnetic resonance analysis and elemental analysis.

EXAMPLE 4

This relates to preparation of the compound:

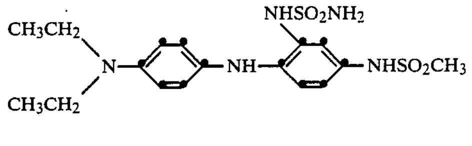

3 grams of the compound prepared in Example 3 were added to 25 milliliters of trifluoroacetic acid at 5° C. under nitrogen and allowed to come to room temperature (about 20° C.) over a 4 hour period. This layer chromatographic analysis indicated an incomplete reaction therefore stirring was continued overnight. The resulting mixture was then poured into an ice water-ethyl acetate mixture and stirred with potassium bicarbonate. The ethyl acetate layer was then washed with saturated aqueous sodium bicarbonate, washed 3 times with water and dried. Solids weighing 2.0 grams resulted having a melting point of 178° C. The desired product was identified by thin layer chromatographic analysis providing one major magenta dye forming component. The desired product was also identified by nuclear magnetic resonance analysis and elemental analysis.

EXAMPLE 5

This relates to preparation of the compound:

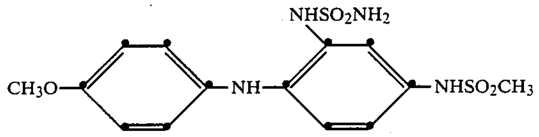

Three grams of 4-methoxy-2'-N-(t-butylsulfamyl-)amino-4'-methanesulfonamidodiphenylamine were added portionwise to 35 milliliters of trifluoroacetic acid with ice water cooling and under nitrogen. Stirring was continued for 4 hours at room temperature (about 20° C.) until thin layer chromatographic analysis indicated the reaction had ceased. Excess trifluoroacetic acid was removed using water aspiration and the residue then triturated with ethyl acetate saturated sodium bicarbonate and ice. The ethyl acetate extract was then washed 3 times with saturated sodium bicarbonate and 3 times with water. The product was then dried and concentrated. The product was then recrystallized from about 15 milliliters of ethyl acetate and 5 milliliters dichloromethane to provide a light pink solid weighing 1.4 grams and having a melting point of 138°-140° C. The desired product was identified by thin layer chromatographic analysis indicating one major red dye

| Component | Coverage |
|---|---|
| diphenylamine: | 0.391 g |
| 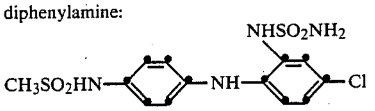 | |
| tetrahydrofuran (solvent) | 0.2 g |
| acetone (solvent) | 1.0 g |
| phthalazinone (toner) | 0.002 g |
| $HgCl_2$ in one drop tetrahydrofuran (antifoggant) | 0.000125 g |
| Solution containing: 0.6 g acetone, 0.4 g of AgBrI (0.04 micron grain size) dispersed in poly(vinyl butyral) (binder) and 1.0 g of silver behenate dispersed in poly(vinyl butyral) | 2 g |

The resulting photothermographic layer was permitted to dry and then overcoated with a 2 mil (50.8 microns) wet coating thickness of poly(isobutylene) (5% by weight) in hexane. The resulting overcoat layer was also allowed to dry.

The resulting photothermographic element was preheated for 2 seconds at 100° C. and then imagewise exposed to light for $10^{-3}$ seconds in a commercial sensitometer to provide a developable latent image in the photothermographic layer. The resulting exposed photothermographic element was then laminated at 135° C. to an amine responsive imaging film containing a cobalt(III) complex. The amine responsive imaging film was prepared as follows:

The following composition was mixed and coated on a subbed poly(ethylene terephthalate) film support to provide the following coverages:

| Component | Coverage in $mg/dm^2$ |
|---|---|
| poly(ethylene-co-1,4-cyclohexylenedimethylene-1-methyl-2,4-benzenedisulfonamide) (binder) | 75.6 |
| phthalalaldehyde (dye former) | 25.1 |
| cobalt(III) hexammine trifluoroacetate | 12.5 |
| surfactant (SF-1066, which is a polysiloxane and is a trademark of an available from the General Electric Co., U.S.A.) | 3.8 |

The resulting amine responsive imaging layer was dried and then overcoated with a composition containing cobalt(III) hexammine trifluoroacetate at 10.8 $mg/dm^2$ and poly(acrylamide-co-N-vinyl-2-pyrrolidone-co-2-acetoacetoxyethyl methacrylate) at 21.5 $mg/dm^2$.

After lamination, the resulting sandwich was heated at 150° C. for 10 seconds. The resulting amine responsive imaging element after processing contained a black image corresponding to the metallic silver image. The phenazine dye produced in the photothermographic layer was produced at 115° C. and absorbed only in the near ultraviolet. This was an advantage because it eliminated a potential visible dye stain problem from integral imagimg materials. The black dye image resulting in the cobalt containing layer had a neutral maximum density of 2.77 and minimum density of 0.05. The image in the photothermographic layer had a neutral maximum density of 1.56 and a minimum density of 1.21.

A strip of the photothermographic element when preheated, imagewise exposed and processed similarly had a neutral maximum density of 0.96 and a minimum density of 0.05.

EXAMPLE 21

Hydrophilic Photothermographic Material

The following components were mixed and coated at a 2 mil (50.8 microns) wet coating thickness on a gel subbed poly(ethylene therephthalate) film support and permitted to dry:

| Component | Concentration |
|---|---|
| Diphenylamine: | 0.219 g |
| 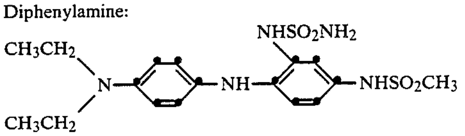 | |
| Methyl urea (melt former) | 0.20 g |
| Water | 2.60 g |
| Deionized gelatin (10% by weight in water) (binder) | 1.0 g |
| Glacial acetic acid (added dropwise with stirring and heating) | 2 drops |
| 0.24 micron silver chloride gelatino emulsion (0.516 grams contained about 98 mg of silver) | 0.516 g |

The resulting photothermographic layer was overcoated with cellulose acetate ((2 mil (50.8 microns) wet coating thickness)) (5% by weight in dichloromethane).

The resulting photothermographic element was imagewise exposed in a commercial graphic arts exposing apparatus containing a quartz halogen lamp (10 seconds using an on/off type of test target) to provide a developable latent image in the photothermographic layer. The exposed photothermographic element was then laminated in face-to-face relation to an amine responsive imaging element as described in Example 19 at 130° C. The resulting sandwich was then processed at 130° C. for 10–15 seconds. A black image was produced in the image receiver that corresponded to the image produced in the photothermographic layer. The photothermographic layer contained a phenazine dye and metallic silver image.

The invention has been described in detail with particular reference to preferred embodiments thereof, but it will be understood that variations and modifications can be effected within the spirit and scope of the invention.

What is claimed is:

1. A diphenylamine selected from the group consisting of:

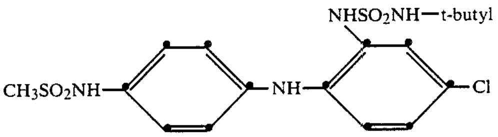

(A)

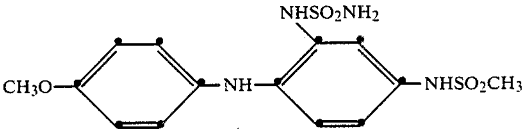

(B)

The resulting composition containing the color-forming diphenylamine and other components of the photothermographic composition was coated on the poly(ethylene terephthalate) support. The resulting coating was permitted to dry and then was overcoated with a 2 mil (50.8 microns) wet coating thickness of 3 weight percent water soluble cellulose acetate as a protective layer.

The resulting photothermographic film was imagewise exposed for $10^{-3}$ seconds in a commercial sensitometer to provide a developable latent image in the photothermographic layer. The exposed photothermographic layer was placed in face-to-face contact with an overcoated amine responsive imaging film and laminated to it by passing the resulting sandwich through heated rollers at 130° C. at 10 pounds/inch$^2$ (68.95 kPa) pressure.

The amine responsive imaging film was prepared by mixing the following components and coating the resulting composition on a subbed poly(ethylene terephthalate) film support at the coverages indicated as follows:

| Component | Coverage (Milligrams Per Square Decimeter) |
|---|---|
| poly(ethylene-co-1,4-cyclohexylenedimethylene-1-methyl-2,4-benzenedisulfonamide) (binder) | 75.6 |
| orthophthalaldehyde | 25.1 |
| cobalt(III) hexammine trifluoroacetate | 12.5 |
| phthalic acid | 0.108 |

Following the lamination step the amine responsive imaging film was separated from the photothermographic layer and heated for 60 seconds at 150° C. A black image resulted in the amine responsive imaging film. The black image corresponded to the silver image in the photothermographic material. The magenta-tinted silver image in the photothermographic layer had a maximum density of 2.73 and a minimum density of 0.40 (both measured as density to green light). The image produced in the amine responsive imaging film containing the cobalt(III) complex had a maximum density of 1.75 and a minimum density of 0.03 (neutral density). The image in the amine responsive imaging film was neutral (black).

EXAMPLE 19

Use of Ammonia Release

A photothermographic silver halide element was prepared by coating the following components on a subbed poly(ethylene terephthalate) film support at a wet coating thickness of 4 mils (101.6 microns) and drying the resulting layer:

| Component | Concentration |
|---|---|
| diphenylamine (color-forming diphenylamine): 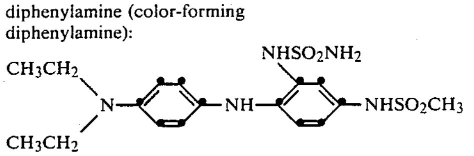 | 0.033 g |
| N—propyl urea (melt former) | 0.025 g |

-continued

| Component | Concentration |
|---|---|
| tetrahydrofuran (solvent) | 0.1 g |
| acetone (solvent) | 0.5 g |
| 5-amino-1,3,6-thiadiazole-2-thiol (development accelerator) in 1 drop tetrahydrofuran | 0.00025 g |
| 1,5-dimethyl-6-allyl-1,2,4-triazolium-3-thiolate (development accelerator) in 1 drop dimethyl formamide | 0.00025 g |
| poly(vinyl butyral) (10% by weight in toluene) (BUTVAR B-76) | 0.3 g |
| silver dodecyltetrazolate dispersion* | 0.7 g |
| silver bromoiodide poly(vinylbutyral) (emulsion) (prepared as described in Example 18) | 0.3 g |

*The silver dodecyltetrazolate dispersion was prepared by ball milling 8.6 grams of the 1:1 silver-dodecyltetrazole complex for one week in 112 grams of 4.46 weight percent of poly(vinylbutral) (BUTVAR B-76) in toluene.

The resulting photothermographic layer was permitted to dry and then overcoated with a 2 mil (50.8 microns) wet coating thickness of poly(isobutylene) 5% by weight in ligroin (boiling point 90°-110° C.) (Vistanex MML 140, which is a trademark of and available from Enjay Chemical Company, U.S.A.). The resulting overcoat layer was also allowed to dry. The resulting photothermographic element was imagewise exposed to light in a commercial sensitometer to provide a developable latent image in the photothermographic layer. The resulting exposed photothermographic element was then laminated to an amine responsive imaging film prepared as follows:

The following composition was mixed and coated on a subbed poly(ethylene terephthalate) film support to provide the following coverages:

| Component | Coverage |
|---|---|
| poly(ethylene-co-1,4-cyclohexylene-dimethylene-1-methyl-2,4-benzene-disulfonamide) (binder) | 75.6 mg/dm$^2$ |
| ortho-phthalaldehyde | 25.1 mg/dm$^2$ |
| cobalt(III) hexammine trifluoroacetate | 12.5 mg/dm$^2$ |

The resulting amine responsive imaging film layer was overcoated with poly(acrylamide-co-N-vinyl-2-pyrolidinone-co-2-acetoacetoxyethylmethacrylate) (about 21.6 mg/dm$^2$). The overcoat contained about 3.2 mg/dm$^2$ of cobalt(III)hexammine trifluoroacetate.

After lamination at 135° C. at 10 psi (68.95 kPa) the resulting sandwich was heated at 140° C. for 10 seconds. The black image in the amine responsive imaging film corresponded to the metallic silver image plus redish dye image in the photothermographic layer. The silver plus dye image in the photothermographic layer had the following densities to green light: Dmax of 0.94, Dmin of 0.37. The image produced in the amine responsive imaging film layer had the following neutral (black) densities: Dmax of 3.3, Dmin of 0.09.

EXAMPLE 20

Another Amine Releasing Compound

A photothermographic silver halide element was prepared by mixing and then coating the following components on a subbed poly(ethylene terephthalate) film support at a wet coating thickness of 4 mils (101.6 microns) and drying the resulting layer:

-continued
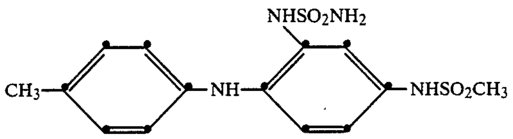
(C)
-continued
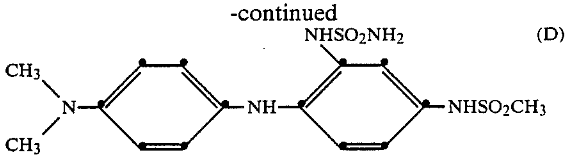
(D)
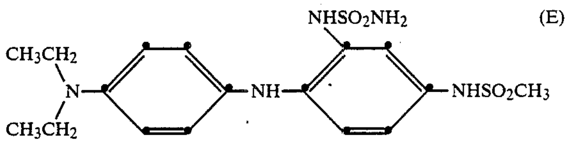
(E)
and combinations thereof.
* * * * *